US009592423B2

United States Patent
Li et al.

(10) Patent No.: US 9,592,423 B2
(45) Date of Patent: Mar. 14, 2017

(54) MEASURING SYSTEM AND MEASURING METHOD FOR ANALYZING KNEE JOINT MOTION TRAJECTORY DURING CYCLING

(71) Applicant: GLOBAL ACTION INC., Taipei (TW)

(72) Inventors: Po-Shin Li, Changhua County (TW); Yu-Shin Chang, Nantou (TW); Keh-Tao Liu, Taipei (TW); Sai-Wei Yang, Taipei (TW)

(73) Assignee: GLOBAL ACTION INC., Taipei (TW)

( * ) Notice: Subject to any disclaimer, the term of this patent is extended or adjusted under 35 U.S.C. 154(b) by 314 days.

(21) Appl. No.: 14/523,455

(22) Filed: Oct. 24, 2014

(65) Prior Publication Data
US 2015/0116472 A1 Apr. 30, 2015

(30) Foreign Application Priority Data

Oct. 24, 2013 (TW) .............................. 102138527 A (51) Int. Cl.
*A43B 7/14* (2006.01)
*A43D 1/02* (2006.01)
(Continued)

(52) U.S. Cl.
CPC ............ *A63B 24/0006* (2013.01); *A43B 7/14* (2013.01); *A43D 1/02* (2013.01); *A61B 5/1114* (2013.01);
(Continued)

(58) Field of Classification Search
CPC ........ A63B 24/0006; A43B 7/14; A43D 1/02; A61B 5/1122; G06K 9/00342; G06T 7/204
(Continued)

(56) References Cited

U.S. PATENT DOCUMENTS 8,567,080 B2 * 10/2013 Yang ........................ A43D 1/02
33/512
9,245,180 B1 * 1/2016 Hansen .............. G06K 9/00362
(Continued)

FOREIGN PATENT DOCUMENTS

KR 101377571 B1 * 3/2014 ............... A61B 5/11

OTHER PUBLICATIONS

("The Effect of Varus and Valgus Wedges on Coronal Plane Knee Motion During Steady-Rate Cycling"); Clinical Journal of Sport Medicine 4:120-124; 1994.*

*Primary Examiner* — William C Vaughn, Jr.
*Assistant Examiner* — Jae N Noh
(74) *Attorney, Agent, or Firm* — Muncy, Geissler, Olds & Lowe, P.C.

(57) ABSTRACT

A measuring system for analyzing a knee joint motion trajectory when a rider is riding a bike (cycling) and a measuring method thereof are disclosed. The measuring system includes a pedal-able device, a light emitting component fixed at a tibial plateau of the rider, an image capturing device, and a knee joint motion trajectory analysis device. When the rider continuously pedals the pedal-able device, the image capturing device captures an image of a central position of the rider's lower limb and a light spot trajectory image of the light emitting component. The motion trajectory analysis device generates an ellipse motion trajectory diagram. After comparing and analyzing a body central line with a trajectory long axis line, a foot force distribution and a shifting data of the knee joint motion trajectory is acquired, and a proper insole is determined.

21 Claims, 8 Drawing Sheets

(51) Int. Cl.
*A63B 24/00* (2006.01)
*A61B 5/11* (2006.01)
*A61B 5/00* (2006.01)
*G06T 7/20* (2006.01)
*G06K 9/00* (2006.01)

(52) U.S. Cl.
CPC .......... *A61B 5/1122* (2013.01); *A61B 5/1127* (2013.01); *A61B 5/4585* (2013.01); *G06K 9/00342* (2013.01); *G06T 7/204* (2013.01); *G06T 2207/10004* (2013.01); *G06T 2207/10152* (2013.01); *G06T 2207/30196* (2013.01); *G06T 2207/30221* (2013.01)

(58) Field of Classification Search
USPC .......................................................... 348/77
See application file for complete search history.

(56) References Cited

U.S. PATENT DOCUMENTS

| | | | | |
|---|---|---|---|---|
| 9,381,417 B2 * | 7/2016 | Inoue | .................... | A61B 5/1127 |
| 2010/0076721 A1 * | 3/2010 | Simms | ................. | A61B 5/1127 |
| | | | | 702/155 |
| 2013/0196829 A1 * | 8/2013 | Elbaz | ....................... | A43B 5/00 |
| | | | | 482/79 |
| 2014/0379135 A1 * | 12/2014 | Kristiansen | ........ | A63B 22/0046 |
| | | | | 700/275 |

\* cited by examiner

MEASURING SYSTEM AND MEASURING METHOD FOR ANALYZING KNEE JOINT MOTION TRAJECTORY DURING CYCLING

BACKGROUND

1. Technical Field

The present disclosure relates to a measuring system and a measuring method for analyzing a knee joint motion trajectory; in particular, to a measuring system and a measuring method utilizing a pedal-able device, and the measuring system and the measuring method capable of generating a light spot trajectory when the rider continues pedaling the pedal-able device, and analyzing the features of the knee joint motion trajectory according to the curves of the light spot trajectory, in order to determine the type of the insole which is suitable to the rider.

2. Description of Related Art

Generally, for allowing the rider to ride a bike in the most comfortable way, a bike fitting process may be necessary for assisting the rider to select the suitable frame size of the bike and select the appropriate accessories of the bike. Thus, the changeable modules of the bike can be adjusted according to the stature and actions of the rider by using the bike fitting processes, for helping suggest the proper riding postures of the rider.

The common bike fitting processes are for adjusting the position of seat and handlebar as well as the posture of the rider to achieve the goal of the rider comfortably reaching the relatively fastest riding speed when riding a bike. The bike fitting processes include, for example, the joint angle analysis (quantifies the stretching and flexing angles), the stability analysis (quantifies the shaking distance), the intensity analysis (quantifies the output power), and the muscle strength analysis (quantifies the posture angle), all of which are all for more properly selecting gears, enabling better gear adjustments, and correctly suggesting the resistance training (weight training) of each body part of the rider. Besides the aforementioned body-related data quantification after the measuring thereof, the biking fitting processes also include adjusting the height of the seats for making the rider to ride in the comfortable way.

The conventional bike fitting processes measure the parameters of the body geometry according to the 2D side view, such as the flexing angles of the elbow, the trunk, the thighs, and the lower limbs. However, the results derived from the simple 2D side view may have some deficiencies. Especially, the conventional bike fitting processes cannot acquire information about the motion stability of the knee joint and the relations between the foot and knee. Therefore, if a measuring system and a measuring method for analyzing the knee joint motion trajectory which can form a 3D measuring system by adding the front view data are provided, the motion stability of the knee joint and the relations between the foot and knee may be obtained by measuring the knee joint motion trajectory when the rider is riding the bike. In addition, the measuring system and method can further determine the proper insole for the rider according to the analysis of the knee joint motion trajectory, and a shoe wedge insert can also be applied for adjusting the motion stabilities of the knee and foot.

SUMMARY

The present disclosure provides a measuring system for analyzing a knee joint motion trajectory during cycling and a measuring method thereof, which can simply and rapidly analyze the knee joint motion trajectory associated with the cycling.

The present disclosure provides a measuring system for analyzing a knee joint motion trajectory during the cycling and a measuring method thereof, which can further determine a proper insole for the rider according to the knee joint motion trajectory associated with the cycling, for adjusting the stabilities of the foot and knee of the rider.

The disclosed measuring system includes a pedal-able device, which may be implemented in terms of a frame having a frame stem and a pair of pedals, for allowing the rider to place his or her feet on the pedals when pedaling. The measuring system further includes a light emitting component which is fixed at a tibial plateau of the lower limb of the rider, for emitting lights when the rider repeatedly pedals the pedal-able device. The measuring system further includes an image capturing device disposed at the front of the pedal-able device, for capturing an image of a central position of the lower limb of the rider and a light spot trajectory image of the light emitting component when the rider repeatedly pedals the pedal-able device. The measuring system further includes a knee joint motion trajectory analysis device connected with the image capturing device. The image capturing device can input the image of the central position of the rider's lower limb and the light spot trajectory image to the knee joint motion trajectory analysis device. The knee joint motion trajectory analysis device includes a trajectory long axis analysis module, for capturing two points which can form the longest line from the upper side and the lower side of the light spot trajectory image. The two points captured at the upper and the lower sides in the light spot trajectory image include an upper limiting point and a lower limiting point, respectively, and can be linked and measured for acquiring a length of a trajectory long axis line. The knee joint motion trajectory analysis device further includes a trajectory transverse line analysis module, for capturing two points from the right side and the left side of the light spot trajectory image. The two points captured from the right side and the left side of the light spot trajectory image can be linked and measured, for acquiring a length of a maximum transverse line. The knee joint motion trajectory analysis device further includes a trajectory tilting angle analysis module connected with the trajectory long axis analysis module. The trajectory tilting angle analysis module can define a reference line which is absolutely vertical to the ground, and analyzes the angle between the reference line and the trajectory long axis line, for acquiring a trajectory tilting angle value. The knee joint motion trajectory analysis device further includes a body central line definition module, for defining a body central line of the rider according to the image of the central position of the rider's lower limb. The knee joint motion trajectory analysis device further includes a motion trajectory analysis module connected with the trajectory long axis analysis module, the trajectory transverse line analysis module, the trajectory tilting angle analysis module, and the body central line definition module, for acquiring an ellipse motion trajectory diagram according to the trajectory long axis line, the maximum transverse line, and the trajectory tilting angle value. The motion trajectory analysis module can also acquire a foot force distribution and a shifting data of the knee joint motion trajectory when the rider is riding the bike by comparing and analyzing the body central line of the rider and the trajectory long axis line of the ellipse motion trajectory diagram. The knee joint motion trajectory analysis device further includes an insole selection determining module connected with the motion trajectory analysis module, for determining the proper foot arch support insole of the rider according to the foot force distribution and the shifting data of the knee joint motion trajectory analyzed by the motion trajectory analysis module.

Specifically, the knee joint motion trajectory analysis device further includes a foot position definition module connected with the motion trajectory analysis module. The foot position definition module can virtually separate the foot of the rider into a left foot part and a right foot part according to the image of the central position of the rider's lower limb, and the foot sole of the right foot part or the left foot part can further be defined. Moreover, an inner side and an outer side of the foot sole can also be defined.

Specifically, the motion trajectory analysis module sets the body central line of the rider as a basis. By analyzing the directions from the upper limiting point to the lower limiting point, if a horizontal projection line of the trajectory long axis line is close to the body central line, the motion trajectory analyzing module can determine whether the foot force distribution slants toward the outer side of the foot sole.

Specifically, if the foot force distribution slants toward the outer side of the foot sole, the insole selection determining module may determine and select the foot arch support insole with relatively smaller rigidity, for allowing the foot force distribution to be adjusted back to the middle, and for offsetting the foot force distribution slanting toward the outer side of the foot sole.

Specifically, the motion trajectory analysis module sets the body central line of the rider as a basis. Analyzing the directions from the upper limiting point to the lower limiting point, if a horizontal projection line of the trajectory long axis line deviates from the body central line, the motion trajectory analyzing module can determine that the foot force distribution slants toward the inner side of the foot sole.

Specifically, if the foot force distribution slants toward the inner side of the foot sole, the insole selection determining module may determine and select the foot arch support insole with relatively larger rigidity, for allowing the foot force distribution to be adjusted back to the middle, and also offsetting the foot force distribution slanting toward the inner side of the foot sole.

Specifically, if the trajectory long axis line of the ellipse motion trajectory diagram is parallel to the body central line, the motion trajectory analyzing module can determine that the foot force distribution is relatively uniform on the pedal. In short, the forces received by the inner side and outer side of the foot sole are substantially the same.

When the forces received by the inner side and outer side of the foot sole are substantially the same, the insole selection determining module may determine and select the foot arch support insole with the moderate rigidity.

Specifically, the light emitting component could be a visible light component or an invisible light component.

In one implementation, the light emitting component is a light emitting diode, that is LED.

The aforementioned measuring method for analyzing the knee joint motion trajectory during the cycling includes the following steps:

1. causing the light emitting component to be fixed at the tibial plateau of the rider's lower limb;
2. capturing the image of the central position of the lower limb of the rider and the light spot trajectory image of the light emitting component by the image capturing device disposed at the front of the pedal-able device when the rider continuously pedals the pedal-able device;
3. analyzing the length of the trajectory long axis line, the length of the maximum transverse line, and the trajectory tilting angle value from the light spot trajectory image, and acquiring the ellipse motion trajectory diagram according to the trajectory long axis line, the maximum transverse line, and the trajectory tilting angle value;
4. defining the body central line of the rider according to the image of the central position of the lower limb of the rider, and acquiring the foot force distribution and the shifting data of the knee joint motion trajectory when the rider is riding the bike by comparing and analyzing the trajectory long axis line of the ellipse motion trajectory diagram on the basis of the body central line; and
5. determining the foot arch support insole suitable to the rider according to the foot force distribution and the shifting data of the knee joint motion trajectory.

Specifically, the mentioned two points captured from the light spot trajectory image could be respectively treated as an upper limiting point and a lower limiting point, and by linking and analyzing the two points from the upper side and the lower side of the light spot trajectory image, the length of the trajectory long axis line can be acquired.

Specifically, the two points could be also considered as the right side and the left side of the light spot trajectory image and linked together before being analyzed. As such, the length of the maximum transverse line may be derived.

Specifically, the trajectory long axis line is analyzed with the reference line which is absolutely vertical to the ground, for acquiring the trajectory tilting angle value.

Specifically, according to the image of the central position of the rider's lower limb, the foot of the rider can be separated into the left foot part and the right foot part. In addition, the foot soles can be further defined from the right foot part and the left foot part, and the inner side and the outer side of the foot sole can also be defined from the foot sole.

Specifically, taking the body central line of the rider as a basis and viewing along the direction from the upper limiting point to the lower limiting point, if the horizontal projection line of the trajectory long axis line is close to the body central line, where the foot force distribution slants toward the outer side of the foot sole can be determined.

Specifically, if the foot force distribution slants toward the outer side of the foot sole, the foot arch support insole with relatively smaller rigidity may be selected, for allowing the foot force distribution to be adjusted back to the middle, and for balancing and adjusting the foot force distribution slanting toward the inner side of the foot sole.

Specifically, taking the body central line of the rider as a basis and viewing along the direction from the upper limiting point to the lower limiting point, if the horizontal projection line of the trajectory long axis line is departs from the body central line, where the foot force distribution slants toward the inner side of the foot sole can be determined.

Specifically, if the foot force distribution slants toward the inner side of the foot sole, the foot arch support insole with relatively larger rigidity is then selected, for allowing the foot force distribution to be adjusted back to the middle, and for balancing and adjusting the foot force distribution slanting toward the outer side of the foot sole.

Specifically, taking the body central line of the rider as a basis, if the trajectory long axis line of the ellipse motion trajectory diagram is parallel to the body central line, that the foot force distribution is relatively uniform and the forces received by the inner side and the outer side of the foot sole are substantially the same may be concluded.

Specifically, if the foot force distribution is relatively uniform and the forces received by the inner side and the outer side of the foot sole are substantially the same the foot arch support insole with moderate rigidity is selected accordingly.

For further understanding of the present disclosure, reference is made to the following detailed description illustrating the embodiments and examples of the present disclosure. The description is only for illustrating the present disclosure, not for limiting the scope of the claim.

BRIEF DESCRIPTION OF THE DRAWINGS

The drawings included herein provide further understanding of the present disclosure. A brief introduction of the drawings is as follows.

DESCRIPTION OF THE EXEMPLARY EMBODIMENTS

The aforementioned and other technical contents, features, and efficacies will be shown in the following detail descriptions of a preferred embodiment corresponding with the reference figures.

Figure 1A:
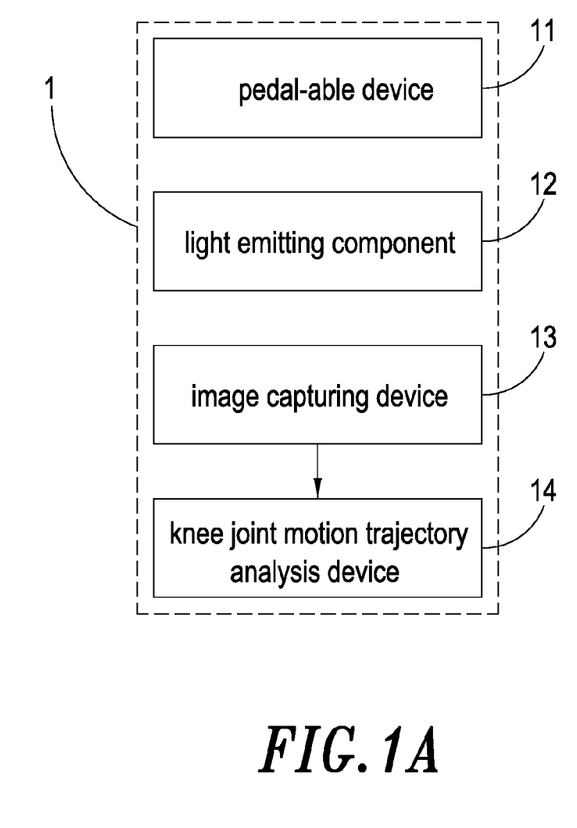
FIG. 1A shows a system structure schematic diagram of a measuring system and a measuring method for analyzing a knee joint motion trajectory during cycling according to one embodiment of the present disclosure.
Figure 1B:
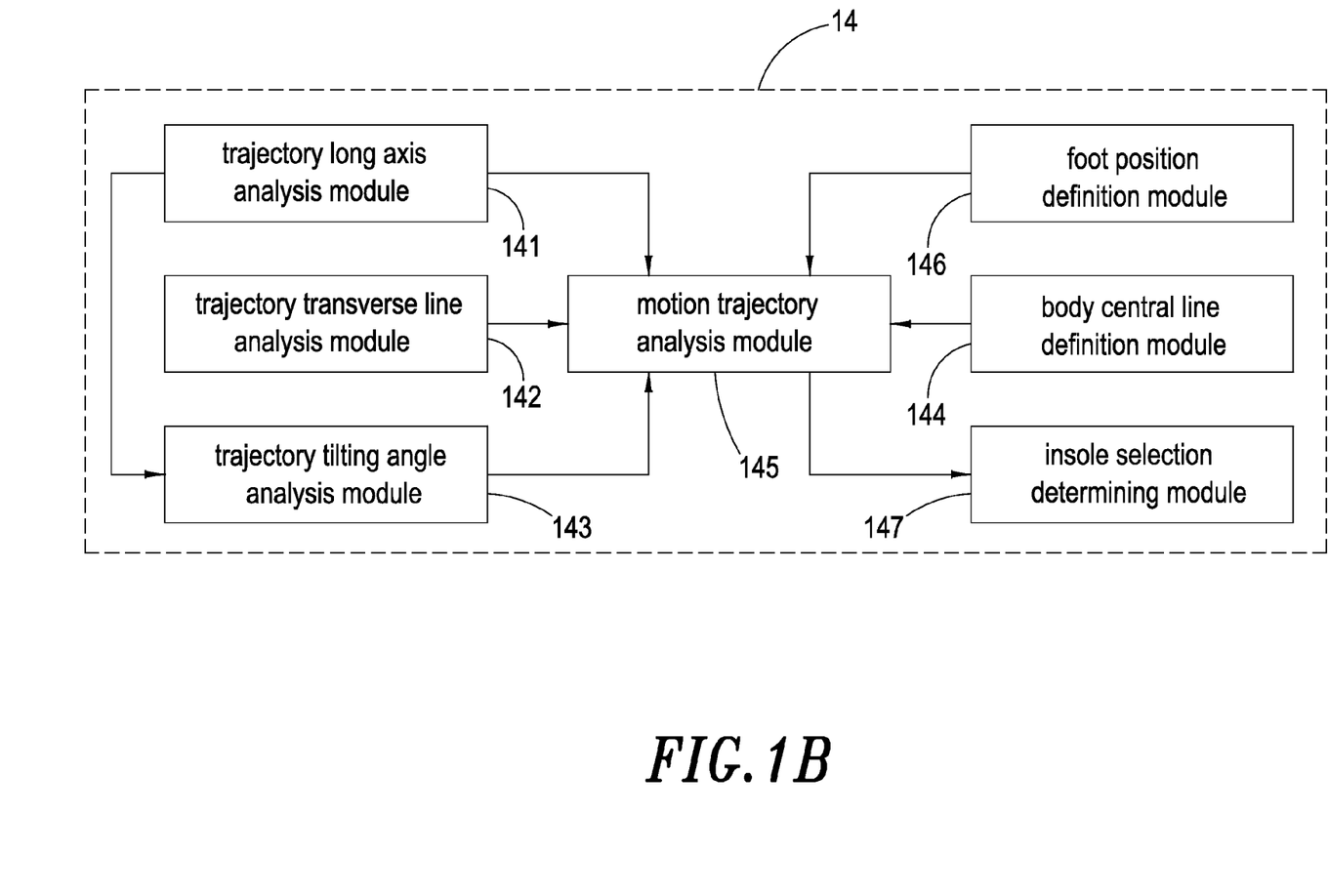
FIG. 1B shows an inner structure schematic diagram of a motion trajectory analysis device of a measuring system and a measuring method for analyzing a knee joint motion trajectory during a cycling according to one embodiment of the present disclosure.

Please refer to FIG. 1A and FIG. 1B which are a system structure diagram and a inner structure diagram of a motion trajectory analysis device of a measuring system and a measuring method for analyzing a knee joint trajectory during cycling according to one embodiment of the present disclosure. The measuring system 1 includes a pedal-able device 11, a light emitting component 12, an image capturing device 13, and a knee joint motion trajectory analysis device 14. In this embodiment, a fixed bike is taken as an example, and the pedal-able device 11 is a frame. The frame includes a frame stem 111 and a pair of pedals 112, for allowing the rider 2 to pedal on the pedals 112.

Figure 2A:
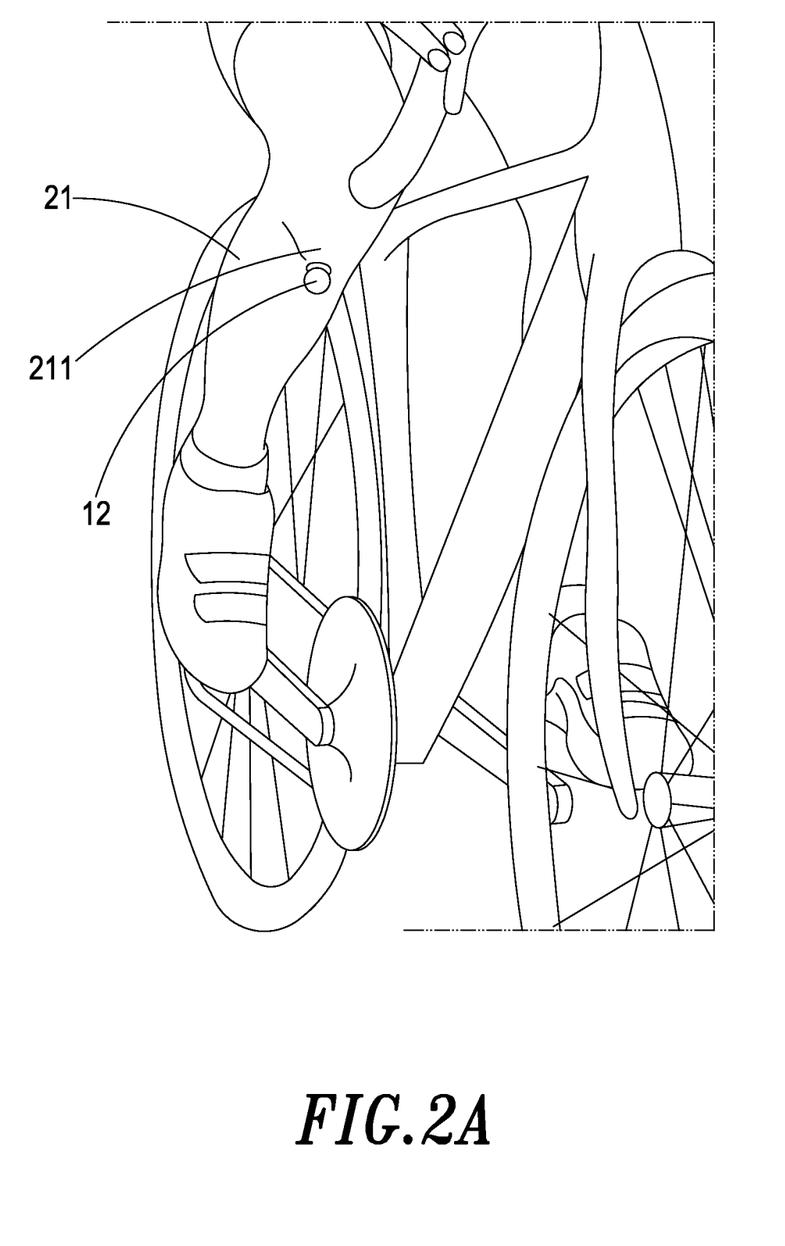
FIG. 2A shows a disposing schematic diagram of a light emitting component of a measuring system and a measuring method for analyzing a knee joint motion trajectory during cycling according to one embodiment of the present disclosure.
Figure 2B:
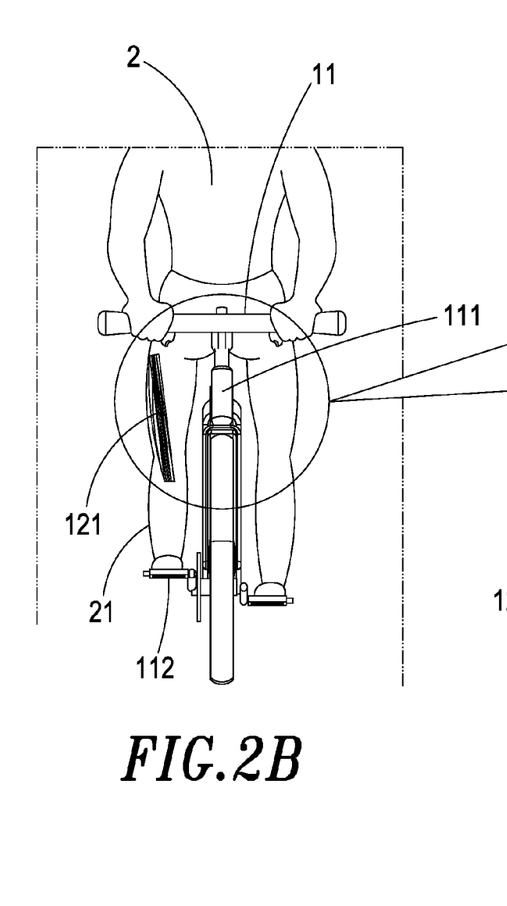
FIG. 2B shows an pedaling image capturing schematic diagram of a measuring system and a measuring method for analyzing a knee joint motion trajectory during cycling according to one embodiment of the present disclosure.
Figure 2C:
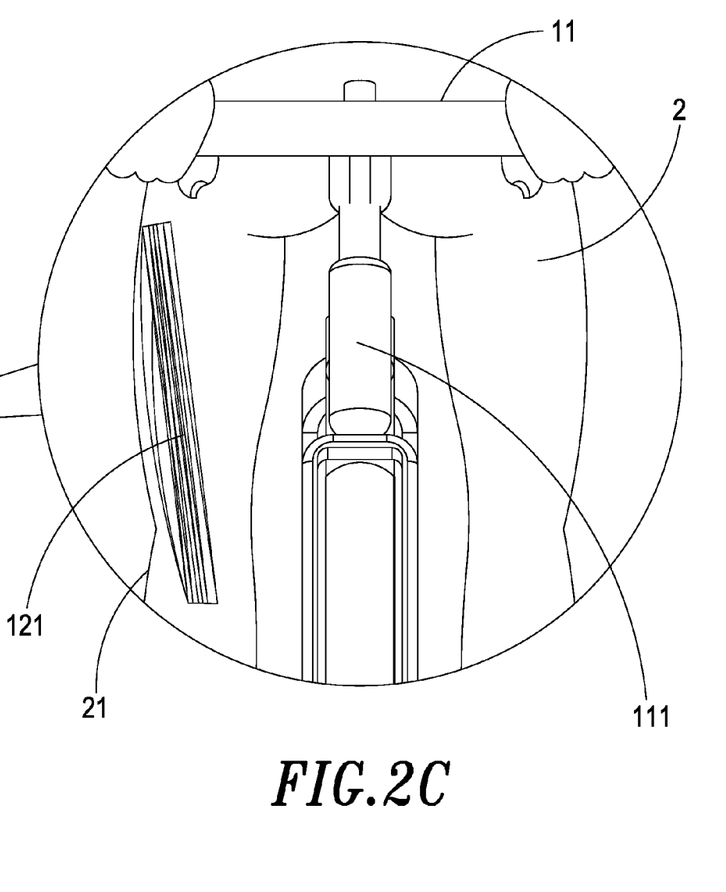
FIG. 2C shows image capturing schematic diagram of a light spot trajectory image of a measuring system and a measuring method for analyzing a knee joint motion trajectory during cycling according to one embodiment of the present disclosure.

The light emitting component 12 (which is, for example, a visible light component or an invisible light component, in this embodiment, the light emitting component 12 is a light emitting diode) is fixed at a tibial plateau 211 of the lower limb 21 of the rider 2 as shown in FIG. 2A. In this embodiment, a Velcro is used for fixing the light emitting component 12 at the tibial plateau 211, though it is well known among the average skilled artisan that other ways could be used to fix the light emitting component 12 to the tibial plateau 211. Thus, when the rider 2 repeatedly pedals on the pedal-able device 11, the light emitting component 12 may emit lights at the same time. Because the image capturing device 13 is disposed at the front of the pedal-able device 11, as shown in FIG. 2B and FIG. 2C, the image capturing device 13 can capture an image of the lower limb 21 of the rider 2 which is relative to the central position of the frame stem 111 and a light spot trajectory image 121 of the light emitting component 12 when the rider 2 rides the bike. For capturing relatively clear light spot trajectory image 121, the image capturing device 13 in this embodiment is a camera. The exposure extension is about 5 seconds, the light intensity is lower than normal indoor living lights, the diaphragm is about F3.5, and the ISO value is preferably ranging from 100 to 400. The parameters of the camera is adjusted instantly according to actual situations, for adjusting and making the captured light spot trajectory image much more clear.

After the image of the lower limb 21 of the rider 2 which is relative to the central position of the frame stem 111 and the light spot trajectory image 121 are captured by the image capturing device 13, they are inputted into the knee joint trajectory analysis device 14 for further analysis. As shown in FIG. 1B, the knee joint trajectory analysis device 14 includes a trajectory long axis analysis module 141, a trajectory transverse line analysis module 142, a trajectory tilting angle analysis module 143, a body central line definition module 144, a motion trajectory analysis module 145, a foot position definition module 146, and an insole selection determining module 147. Two points from the upper side and the lower side of the light spot trajectory image 121 as one longest line can be captured by the trajectory long axis analysis module 141, and are respectively an upper limiting point 14111 and a lower limiting point 14112. The upper limiting point 14111 and the lower limiting point 14112 are linked and measured for acquiring the length of the trajectory long axis line 1411.

After that, two points from the right side and the left side as another longest line of the light spot trajectory image 121 may be captured by the trajectory transverse line analysis module 142, and the two points can be linked and measured for acquiring the length of the maximum transverse line 1421. The trajectory tilting angle analysis module 143 can define a reference line 1431 which is vertical to the ground, and analyzes the angle between the reference line and the trajectory long axis line 1411, for acquiring a trajectory tilting angle value 1432.

Figure 2D:
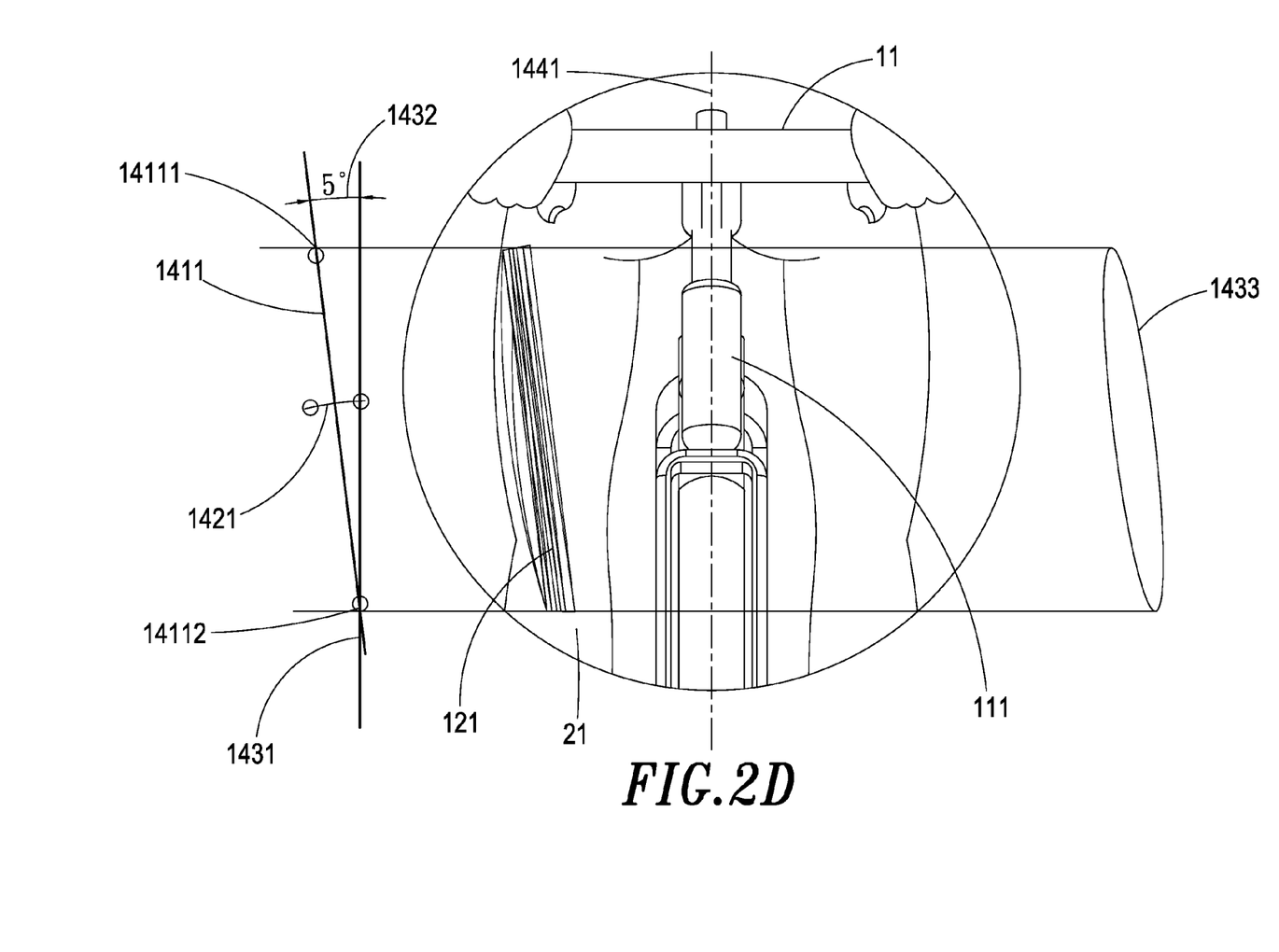
FIG. 2D shows schematic diagram of the forming of an ellipse motion trajectory of a measuring system and a measuring method for analyzing a knee joint motion trajectory during cycling according to one embodiment of the present disclosure.

For comparing and analyzing, a body central line 1441 of the rider 2 is defined by the body central line definition module 144 according to the image of the lower limb 21 of the rider 2. The central line of the frame stem 111 can serve as a reference basis when the body central line 1441 is defined. In general situation, the body central line 1441 of the rider 2 is overlapping with the central line of the frame stem 111. After that, the trajectory long axis line 1411, the maximum transverse line 1421, and the trajectory tilting angle value 1432 are inputted into the motion trajectory analysis module 145, as show in FIG. 2D. The motion trajectory analysis module 145 may generate an ellipse motion trajectory diagram 1433 according to the trajectory long axis line 1411, the maximum transverse line 1421, and the trajectory tilting angle value 1432.

The rider 2 usually has a right foot and a left foot. Thus the feet of the rider 2 may be considered to be separated into a right foot part and a left foot part by the foot position definition module 146 according to the image of the lower limb 21 of the rider 2. The foot soles can be further defined from the right foot part and the left foot part, and an inner side and an outer side can also be defined from the foot sole. Taking the body central line 1441 as a basis, the trajectory long axis line 1411 of the ellipse motion trajectory diagram 1433 is compared and analyzed, for acquiring a foot force distribution and a shifting data of the knee joint motion trajectory. The following description takes the right foot part as an analysis example.

Figure 3A:
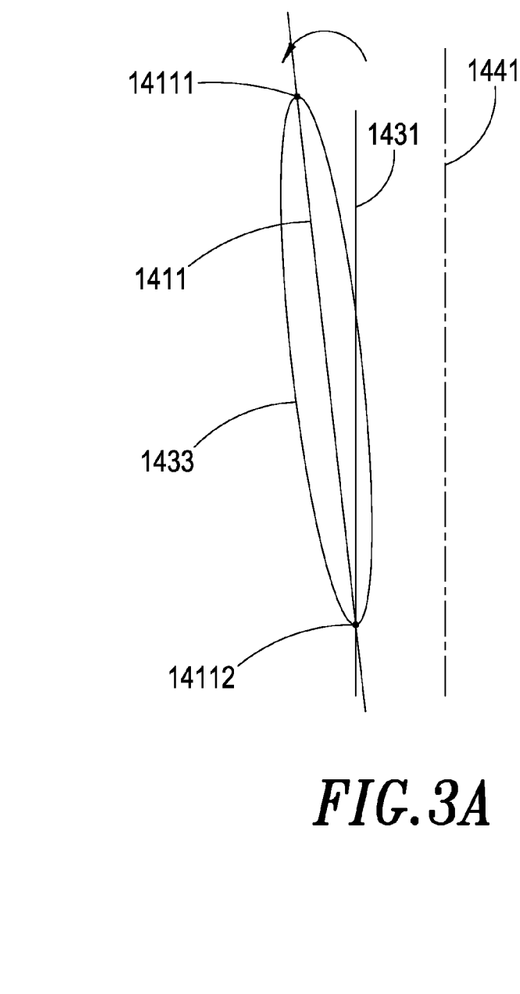
FIG. 3A shows schematic diagram of an ellipse motion trajectory which is tilting toward outside of a measuring system and a measuring method for analyzing a knee joint motion trajectory during cycling according to one embodiment of the present disclosure.
Figure 3B:
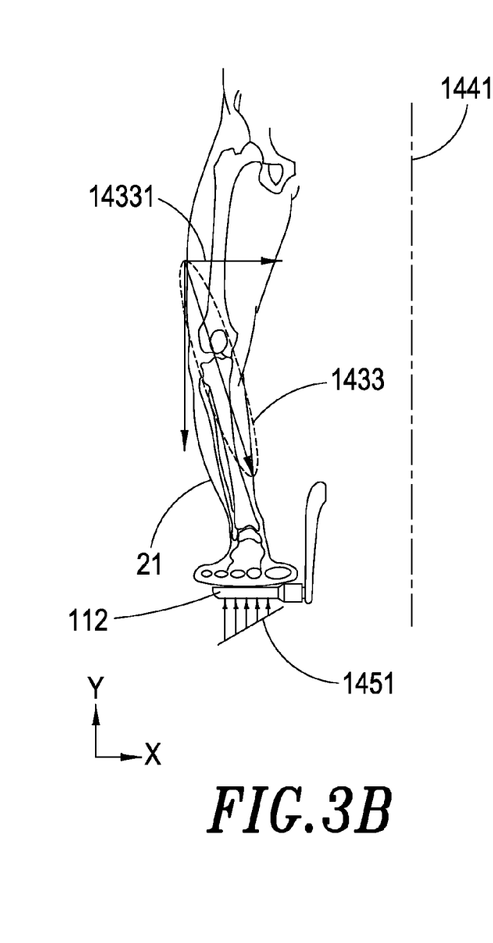
FIG. 3B shows a schematic diagram of a foot force distribution of a measuring system and a measuring method for analyzing a knee joint motion trajectory during cycling according to one embodiment of the present disclosure.

(1) As shown in FIG. 3A, taking the body central line 1441 of the rider 2 as a basis and viewing along the direction from the upper limiting point 14111 to the lower limiting point 14112, the horizontal projection line 14331 of the trajectory long axis line 1411 is close to the body central line 1441. Therefore, the motion trajectory analysis module 145 may conclude that the foot force distribution is slanting toward the outer side of the foot sole. Please refer to FIG. 3B along with FIG. 3A, the foot force distribution slants toward the outer side of the foot sole according to the foot force distribution line 1451. After the foot force distribution and the shifting data of the knee joint motion trajectory are analyzed, an insole suitable to the rider 2 can further be selected. In this case, a foot arch support insole with relatively smaller rigidity is to be selected, enabling the foot force distribution to be adjusted back to the middle, and balancing and adjusting the foot force distribution slanting toward the inner side of the foot sole.

Figure 5A:
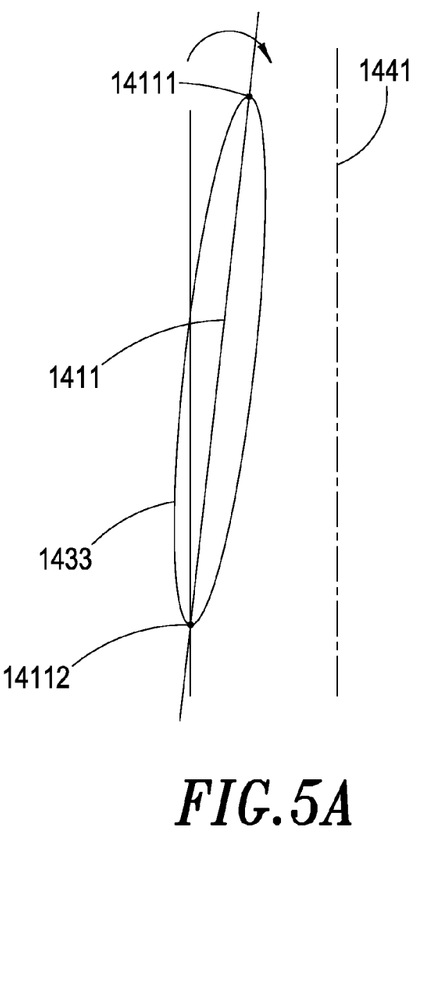
FIG. 5A shows a schematic diagram of an ellipse motion trajectory tilting toward inside of a measuring system and a measuring method for analyzing a knee joint motion trajectory during cycling according to one embodiment of the present disclosure.
Figure 5B:
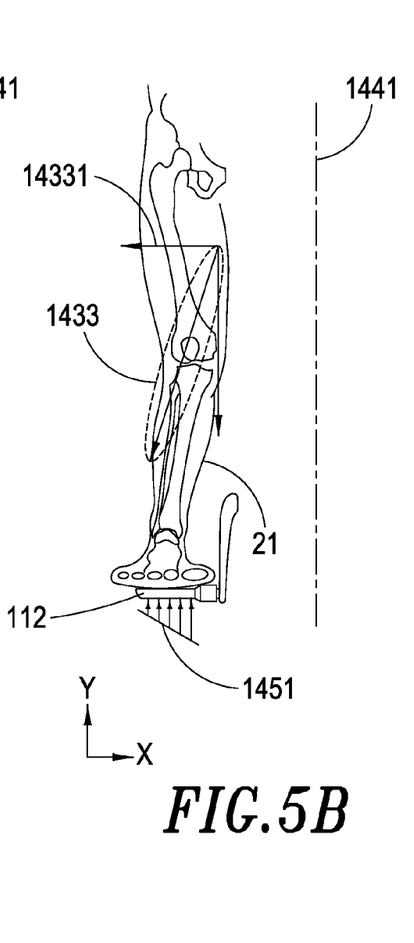
FIG. 5B shows a schematic diagram of a foot force distribution of a measuring system and a measuring method for analyzing a knee joint motion trajectory during cycling according to one embodiment of the present disclosure.

(2) As shown in FIG. 5A, taking the body central line 1441 of the rider 2 as a basis and viewing along the direction from the upper limiting point 14111 to the lower limiting point 14112, the horizontal projection line 14331 of the trajectory long axis line 1411 departs from the body central line 1441. Therefore, the motion trajectory analysis module 145 may determine that the foot force distribution slants toward the inner side of the foot sole. Please refer to FIG. 5B along with FIG. 5A showing the foot force distribution slants toward the inner side of the foot sole according to the foot force distribution line 1451. After the foot force distribution and the shifting data of the knee joint motion trajectory are analyzed, an insole which is suitable to the rider 2 can further be selected. In this case, a foot arch support insole with relatively larger rigidity is selected, for enabling the foot force distribution to be adjusted back to the middle, and for balancing and adjusting the foot force distribution slanting toward the outer side of the foot sole.

Figure 4A:
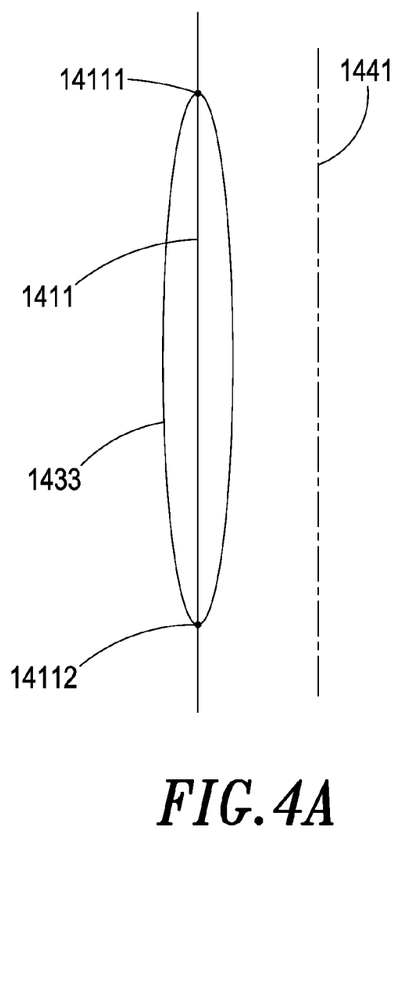
FIG. 4A shows a schematic diagram of an ellipse motion trajectory, which is parallel to the body central line or is vertical to the ground, of a measuring system and a measuring method for analyzing a knee joint motion trajectory during cycling according to one embodiment of the present disclosure.
Figure 4B:
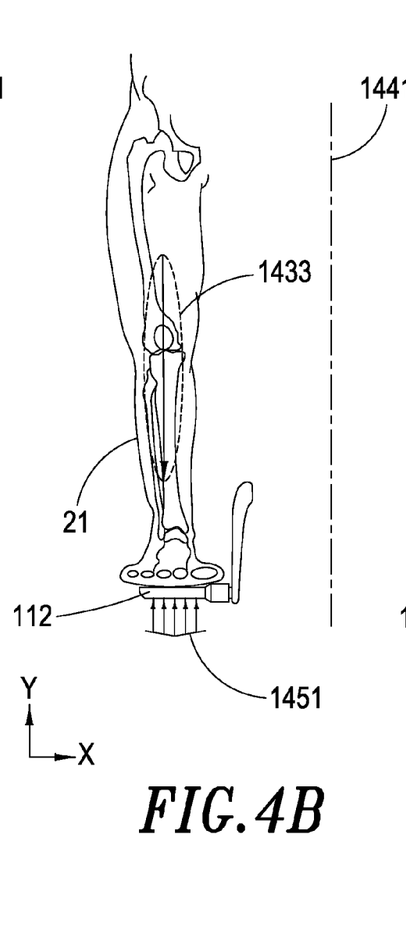
FIG. 4B shows a schematic diagram of a foot force distribution of a measuring system and a measuring method for analyzing a knee joint motion trajectory during cycling according to one embodiment of the present disclosure.

(3) As shown in FIG. 4A, taking the body central line 1441 of the rider 2 as a basis, because the trajectory long axis line 1411 is parallel to the body central line 1441, the motion trajectory analysis module 145 may determine that the foot force distribution is relatively uniform and the forces received by the inner side and the outer side of the foot sole are substantially the same. Please refer to FIG. 4B along with FIG. 4A illustrative of the relative uniform foot force distribution and the inner side and the outer side of the foot sole receiving substantially the same force according to the foot force distribution line 1451. After the foot force distribution and the shifting data of the knee joint motion trajectory are analyzed, an insole which is suitable to the rider 2 can further be selected. In this case, a foot arch support insole with moderate rigidity may be selected.

In addition, the analyses of the left foot part of the rider 2 are similar to the analyses of the right foot part, thus are not repeatedly described.

Figure 6:
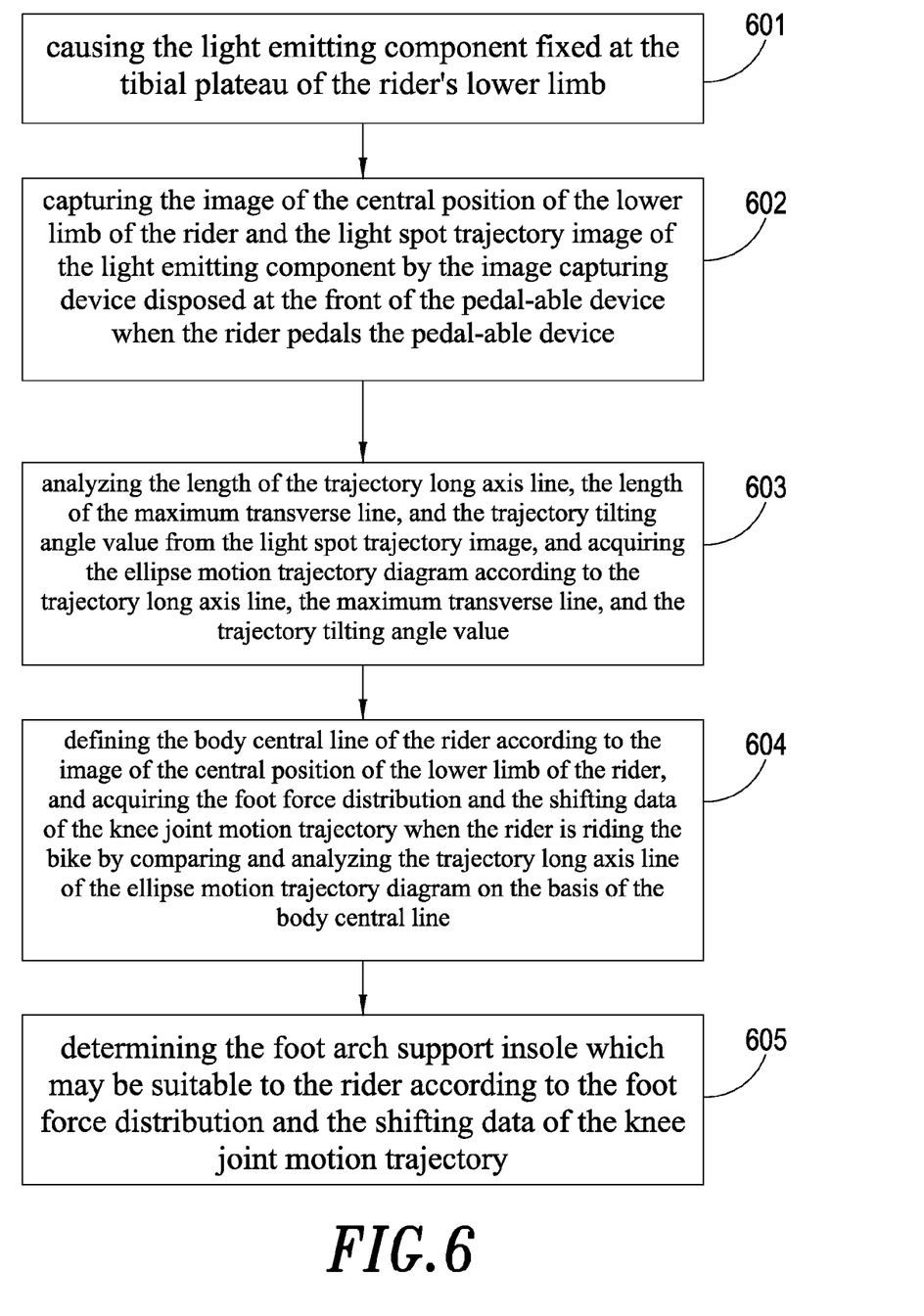
FIG. 6 shows a flow chart of a measuring system and a measuring method for analyzing a knee joint motion trajectory during cycling according to one embodiment of the present disclosure.

On the basis of the above, as shown in FIG. 6, the steps of the measuring method for analyzing the knee joint motion trajectory during the cycling may include:

1. causing the light emitting component fixed at the tibial plateau of the rider's lower limb (601);

2. capturing the image of the central position of the lower limb of the rider and the light spot trajectory image of the light emitting component by the image capturing device disposed at the front of the pedal-able device when the rider pedals the pedal-able device (602);

3. analyzing the length of the trajectory long axis line, the length of the maximum transverse line, and the trajectory tilting angle value from the light spot trajectory image, and acquiring the ellipse motion trajectory diagram according to the trajectory long axis line, the maximum transverse line, and the trajectory tilting angle value (603);

4. defining the body central line of the rider according to the image of the central position of the lower limb of the rider, and acquiring the foot force distribution and the shifting data of the knee joint motion trajectory when the rider is riding the bike by comparing and analyzing the trajectory long axis line of the ellipse motion trajectory diagram on the basis of the body central line (604); and 5. determining the foot arch support insole which may be suitable to the rider according to the foot force distribution and the shifting data of the knee joint motion trajectory (605).

Comparing with other conventional techniques, the measuring system and measuring method for analyzing the knee joint motion trajectory during the cycling according to the present disclosure have the following advantages including rapidly capturing the knee joint trajectory when the rider is riding a bike with ease, and capability of analyzing the trajectory features by using the knee joint trajectory analysis device and selecting the proper insole which is suitable to the rider according to the knee joint motion trajectory, for adjusting the motion stabilities of the feet and knees of the rider.

Some modifications of these examples, as well as other possibilities will, on reading or having read this description, or having comprehended these examples, will occur to those skilled in the art. Such modifications and variations are comprehended within this disclosure as described here and claimed below. The description above illustrates only a relative few specific embodiments and examples of the present disclosure. The present disclosure, indeed, does include various modifications and variations made to the structures and operations described herein, which still fall within the scope of the present disclosure as defined in the following claims.

What is claimed is:

1. A measuring system for analyzing a knee joint motion trajectory for measuring and analyzing the knee joint motion trajectory when a rider is riding a bike, comprising:
    a pedal-able device which is a frame including a frame stem and a pair of pedals, for allowing the rider to place his/her feet on the pedals;
    a light emitting component fixed at a tibial plateau of a lower limb of the rider, for emitting lights when the rider continuously pedals the pedal-able device;
    an image capturing device disposed at the front of the pedal-able device, wherein when the rider continuously pedals the pedal-able device, the image capturing device captures an image including the central position of the lower limb of the rider and a light spot trajectory image of the light emitting component;
    a knee joint motion trajectory analysis device, connected with the image capturing device, wherein the image capturing device inputs the image of the central position of the lower limb of the rider and the light spot trajectory image of the light emitting component to the knee joint motion trajectory analysis device, and the knee joint motion trajectory analysis device includes:
        a trajectory long axis analysis module which captures two points from the upper side and the lower side of the light spot trajectory image as a longest line, wherein the two points are respectively an upper limiting point and a lower limiting point, and by measuring the longest line virtually linked between the two points captured from the upper side and the lower side of the light spot trajectory image, a length of a trajectory long axis line is acquired;
        a trajectory transverse line analysis module which captures two points from the left side and the right side of the light spot trajectory image as another longest line, wherein by measuring the longest line between the two points captured from the right side and the left side of the light spot trajectory image, a length of a maximum transverse line is acquired;
        a trajectory tilting angle analysis module, connected with the trajectory long axis analysis module, wherein the trajectory tilting angle analysis module defines a reference line which is absolutely vertical to the ground, and analyzes an angle between the reference line and the trajectory long axis line for acquiring a trajectory tilting angle value;
        a body central line definition module defining a body central line of the rider according to the image of the central position of the lower limb of the rider;
        a motion trajectory analysis module, connected with the trajectory long axis analysis module, the trajectory transverse line analysis module, the trajectory tilting angle analysis module, and the body central line definition module, wherein the motion trajectory analysis module acquires an ellipse motion trajectory diagram according to the trajectory long axis line, the maximum transverse line, and the trajectory tilting angle value, and after comparing and analyzing the trajectory long axis line of the ellipse motion trajectory diagram on the basis of the body central line of the rider, the motion trajectory analysis module also acquires a foot force distribution and a shifting data of the knee joint motion trajectory when the rider is riding the bike; and
        an insole selection determining module, connected with the motion trajectory analysis module, for determining a foot arch support insole which is suitable to the rider according to the foot force distribution and the shifting data of the knee joint motion trajectory analyzed by the motion trajectory analysis module.

2. The measuring system according to claim 1, wherein the knee joint motion trajectory analysis device further includes a foot position definition module which is connected with the motion trajectory analysis device, the feet of the rider is considered to be a left foot part and a right foot part according to the image of the central position of the lower limb of the rider, two foot soles are respectively defined from the left foot part and the right foot part, and an inner side and an outer side of the foot sole is be defined from the foot sole.

3. The measuring system according to claim 2, wherein the motion trajectory analysis module sets the body central line of the rider as a basis, and when viewed along a direction from the upper limiting point to the lower limiting point if a horizontal projection line of the trajectory long axis line is close to the body central line, the motion trajectory analysis module determines that the foot force distribution slants toward the outer side of the foot sole.

4. The measuring system according to claim 3, wherein if the foot force distribution slants toward the outer side of the foot sole, the insole selection determining module determines and selects the foot arch support insole with relatively small rigidity, for allowing the foot force distribution to be adjusted back to the middle, in order to balance and adjust the foot force distribution slanting toward the inner side of the foot sole.

5. The measuring system according to claim 2, wherein the motion trajectory analysis module sets the body central line of the rider as a basis, and when viewed along the direction from the upper limiting point to the lower limiting point if a horizontal projection line of the trajectory long axis line departs from the body central line, the motion trajectory analysis module determines the foot force distribution slants toward the inner side of the foot sole.

6. The measuring system according to claim 5, wherein if the foot force distribution slants toward the inner side of the foot sole, the insole selection determining module determines and selects the foot arch support insole with a relatively larger rigidity, for allowing the foot force distribution to be adjusted back to the middle, in order to balance and adjust the foot force distribution slanting toward the outer side of the foot sole.

7. The measuring system according to claim 2, wherein the motion trajectory analysis module sets the body central line of the rider as a basis, and if the trajectory long axis line of the ellipse motion trajectory diagram is parallel to the body central line, the motion trajectory analysis module determines that the foot force distribution is relatively uniform and forces received by the inner side and the outer side of the foot sole are substantially the same.

8. The measuring system according to claim 7, wherein if the foot force distribution is relatively uniform and the forces received by the inner side and the outer side of the foot sole are substantially the same, the insole selection determining module determines and selects the foot arch support insole with relatively moderate rigidity.

9. The measuring system according to claim 1, wherein the light emitting component is a visible light component or an invisible light component.

10. The measuring system according to claim 9, wherein the light emitting component is a light emitting diode (LED).

11. A measuring method for analyzing a knee joint motion trajectory when a rider is riding a bike, comprising:
  causing a light emitting component to be fixed at a tibial plateau of a lower limb of the rider;
  capturing an image of a central position of the lower limb of the rider and a light spot trajectory image of the light emitting component by an image capturing device disposed at the front of a pedal-able device when the rider continuously pedals the pedal-able device;
  analyzing a length of a trajectory long axis line, a length of a maximum transverse line, and a trajectory tilting angle value from the light spot trajectory image, and acquiring an ellipse motion trajectory diagram according to the trajectory long axis line, the maximum transverse line, and the trajectory tilting angle value;
  defining a body central line of the rider according to the image of the central position of the lower limb of the rider, and acquiring a foot force distribution and a shifting data of the knee joint motion trajectory when the rider is riding the bike by comparing and analyzing the trajectory long axis line of the ellipse motion trajectory diagram on the basis of the body central line; and
  determining a foot arch support insole suitable to the rider according to the foot force distribution and the shifting data of the knee joint motion trajectory.

12. The measuring method according to claim 11, wherein two points captured from the upper side and the lower side of the light spot trajectory image when connected form a longest line, the two points are respectively an upper limiting point and a lower limiting point, and the length of the trajectory long axis line is acquired by linking the two points captured from the upper side and the lower side of the light spot trajectory image.

13. The measuring method according to claim 11, wherein two points captured from the right side and the left side of the light spot trajectory image when connected together form another longest line, and the length of the maximum transverse line is acquired by linking the two points which are captured from the right side and the left side of the light spot trajectory image.

14. The measuring method according to claim 11, wherein the trajectory long axis line is analyzed with a reference line which is absolutely vertical to the ground, for acquiring the trajectory tilting angle value.

15. The measuring method according to claim 11, wherein feet of the rider is considered to be a right foot part and a left foot part according to the image of the central position of the lower limb of the rider, foot soles is defined from the left foot part and the right foot part, and an outer side and an inner side is defined from the foot sole.

16. The measuring method according to claim 15, further comprising, when taking the body central line of the rider as a basis and viewed along a direction from an upper limiting point to a lower limiting point of the trajectory long axis line, if a horizontal projection line of the trajectory long axis line is close to the body central line, determining the foot force distribution slants toward the outer side of the foot sole.

17. The measuring method according to claim 16, further comprising if the foot force distribution slants toward the outer side of the foot sole, selecting the foot arch support insole with a relatively small rigidity, for allowing the foot force distribution to be adjusted back to the middle, in order to balance and adjust the foot force distribution is slanting toward the inner side of the foot sole.

18. The measuring method according to claim 15, further comprising, when taking the body central line of the rider as a basis and viewed along a direction from an upper limiting point to a lower limiting point of the trajectory long axis line, if a horizontal projection line of the trajectory long axis line departs from the body central line, determining the foot force distribution slants toward the inner side of the foot sole.

19. The measuring method according to claim 18, further comprising if the foot force distribution slants toward the inner side of the foot sole selecting the foot arch support insole with a relatively large rigidity, for allowing the foot force distribution to be adjusted back to the middle, in order to balance and adjust the foot force distribution slanting toward the outer side of the foot sole.

20. The measuring method according to claim 15, further comprising, when taking the body central line of the rider as a basis, if the trajectory long axis line of the ellipse motion trajectory diagram is parallel to the body central line, determining that the foot force distribution is relatively uniform and forces received by the inner side and the outer side of the foot sole are substantially the same.

21. The measuring method according to claim 20, further comprising if the foot force distribution is relatively average and the forces received by the inner side and the outer side of the foot sole are the same selecting a foot arch support insole with a relatively moderate rigidity.

* * * * *